US012056805B1

United States Patent
Lin et al.

(10) Patent No.: US 12,056,805 B1
(45) Date of Patent: Aug. 6, 2024

(54) INTELLIGENT REGULATION AND MANAGEMENT SYSTEM FOR CAR BEAUTY LAMP AND IN-VEHICLE HUMAN BODY BEAUTY LIGHT SOURCE

(71) Applicant: Y.LIN ELECTRONICS CO., LTD., Guangdong (CN)

(72) Inventors: Qicheng Lin, Guangdong (CN); Guoliang Qiu, Miaoli County (TW); Huiyan Zhong, Guangdong (CN); Jiaxin Lai, Guangdong (CN); Hongrui Wu, Guangxi (CN); Huihuang Liu, Hunan (CN); Gangwei Zhang, Guangdong (CN); Zhichao Ye, Guangdong (CN); Yonghan Wu, Fujian (CN); Ming Liu, Jianxi (CN); Zhihao Qiu, Guangdong (CN)

(73) Assignee: Y.LIN ELECTRONICS CO., LTD., Dongguan (CN)

( * ) Notice: Subject to any disclaimer, the term of this patent is extended or adjusted under 35 U.S.C. 154(b) by 0 days.

(21) Appl. No.: 18/423,370

(22) Filed: Jan. 26, 2024

(30) Foreign Application Priority Data

Dec. 29, 2023 (CN) .......................... 202311849730.4

(51) Int. Cl.
G06T 15/00 (2011.01)
A61N 5/06 (2006.01)
G06T 15/04 (2011.01)

(52) U.S. Cl.
CPC .......... *G06T 15/005* (2013.01); *A61N 5/0616* (2013.01); *G06T 15/04* (2013.01)

(58) Field of Classification Search
CPC ...... G06T 15/005; G06T 15/04; A61N 5/0616
See application file for complete search history.

(56) References Cited

U.S. PATENT DOCUMENTS

| 2003/0065589 | A1* | 4/2003 | Giacchetti | G06T 11/00 |
| | | | | 705/26.1 |
| 2019/0335551 | A1* | 10/2019 | Williams | H05B 45/24 |
| 2020/0098444 | A1* | 3/2020 | Tran | G06N 3/08 |

* cited by examiner

Primary Examiner — Michelle Chin (57) ABSTRACT

Disclosed are an intelligent regulation and management system for a car beauty lamp and an in-vehicle human body beauty light source. A technical solution of the present disclosure includes: a data layer and a processing layer are designed based on an NET open source architecture, a database includes a cache of information about the processing layer, a phototherapy laser table and user management information, and the database performs distributed storage and invoking management; a monitoring module constructs an actual three-dimensional skin model of a user based on a facial surface state and a facial skin thickness state of the user, and obtains a facial state index according to an evaluation formula; a determination module selects a working band of the beauty light source; and a regulation layer acquires a simulation temperature value when a light source irradiates facial skin, and controls a working state of the beauty lamp.

9 Claims, 3 Drawing Sheets

FIG. 1

Step S1: Determine whether a user is permitted to log into a system when the user performs user identity identification verification through an automobile central control client or a mobile client, and obtain access right to the corresponding information according to the user's identity Step S2: Construct an actual three-dimensional facial model of the user via a visual scanning device and an ultrasonic measurement device, and divide various parts of the user's face; where a monitoring module obtains a facial state index of a single divided area according to an evaluation formula, a determination module displays different working mode suggestions in a display layer according to the state index, and the user selects a working mode of a beauty lamp according to the suggestions Step S3: In the working process of the beauty lamp, the regulation layer obtains a skin area according to the simulation temperature value of the conduction when the light source irradiates the facial skin and the temperature is too high, and controls the switch of the beauty lamp according to different output results; when the skin area under an excessively high temperature state is less than $m$, the beauty lamp will work normally; and in other cases, the beauty lamp will be turned off Step S4: The display layer displays the completion of working of the beauty lamp

INTELLIGENT REGULATION AND MANAGEMENT SYSTEM FOR CAR BEAUTY LAMP AND IN-VEHICLE HUMAN BODY BEAUTY LIGHT SOURCE

CROSS REFERENCE TO RELATED APPLICATIONS

The present application claims the benefit of Chinese Patent Application No. 202311849730.4 filed on Dec. 29, 2023. All the above are hereby incorporated by reference in their entirety.

TECHNICAL FIELD

The present disclosure relates to the field of laser beauty light sources and control, and more particularly to an intelligent regulation and management system for a car beauty lamp and an in-vehicle human body beauty light source.

BACKGROUND

As laser technology is gradually applied in the field of beauty, and demands of users for beauty and skincare gradually increase, beauty lamps are also integrated in various fields. Among them, the application of the beauty lamps in the automotive industry has become a trend. When a user uses a beauty lamp in the field, ultraviolet rays or environmental conditions are relatively harsh, significant damage, even irreparable harm, will be caused to the user's skin. The damaged skin not only affects the user's psychological state during inspection or field work, but also affects the progress of the work. A car is an indispensable means of transportation; therefore, a car beauty lamp can satisfy a user's skincare demand at any time.

When acting on the human body, lasers from the car beauty lamp will generate heat near the body tissues where the lasers are applied, and concentration of a laser light source will also generate heat, the heat generated therefrom, when being diffused onto the human skin, will form a temperature. However, too high temperature will result in skin burns, which will affect a beauty effect and possibly leads to adverse influence. Furthermore, medical staff or medicines are scarce during the field operation, and the skin burns may affect the subsequent recovery. Therefore, temperature safety protection is required in the working process of the beauty lamp.

SUMMARY

In view of the problems existing in the flow control process of a burner in the prior art, an objective of the present disclosure is to provide an intelligent regulation and management system for a car beauty lamp and an in-vehicle human body beauty light source, so as to achieve skin beauty in a car and safety control of temperature during operation.

In order to achieve the above objective, the present disclosure provides the following technical solution:

An intelligent regulation and management system for a car beauty lamp, including a data layer, a processing layer, a regulation layer and a display layer;

the data layer includes a database and an invoking group, where the data layer and the processing layer are designed based on an NET open source architecture, the database includes a cache of information about the processing layer, a phototherapy laser table and user management information, the phototherapy laser table includes laser wave bands corresponding to each phototherapy, and the database performs distributed storage and invoking management;

the processing layer includes a monitoring module and a determination module, where the monitoring module constructs an actual three-dimensional skin model of a user based on a skin surface state of and a skin thickness state of the user, and acquires a skin state index of a single divided region according to an evaluation formula, so as to provide data support for determination of the determination module; and the determination module determines whether the beauty lamp is suitable for working according to the determination results;

the regulation layer acquires a simulation temperature value of the conduction when a light source irradiates facial skin based on a nonlinear transient heat conduction model constructed through a light-heat source model, and controls a working state of the beauty lamp; and the display layer is configured to input and output an application instruction, and display a page terminal.

Preferably, the user management information includes a sample pre-stored by the user; the sample is a standard three-dimensional skin model, where the sample includes the skin surface state and the skin thickness state of the user in the most ideal state, and in which case, the skin surface state includes wrinkles, spots and pores; and the skin thickness is only used for calculating a loss state of a collagen layer.

The user management information further includes user identity authentication and permission management, where the user identity authentication is used for user login, and the invoking group checks the identity information inputted by the user when the user logs in against the identity information stored in the database to determine whether the user has the login permission; and the permission management limits the user's access content through a permission model, and assigns corresponding data groups according to the user's authentication identity.

The monitoring module is connected to a monitoring device, and the monitoring module receives facial images of the user in the monitoring device; the monitoring device includes a visual scanning device and an ultrasonic measurement device, where the visual scanning device includes a 4D optical imaging of human skin, and completes image shooting including pores, skin lines and wrinkles through a rapid optical non-contact skin imaging system; and the monitoring module is configured to acquire skin states or various parts of the user's face, and specific working process of the monitoring module includes the following steps:

Step S31: the scanning model scans a facial surface state of the user, the ultrasonic measurement device measures a facial skin thickness state of the user, and images of the facial surface state and the facial skin thickness state of the user are combined to construct an actual three-dimensional facial model of the user;

Step S32: the monitoring module divides each part of the face based on the actual three-dimensional facial model of the user, it is set that there are n divided areas, and any of the divided areas is marked with i, then means an area divided by the i area;

Step S33: the monitoring module compares the actual three-dimensional skin model of the divided areas with samples in the database, and performs correlation extraction and processing on surface state images of the face according to the detection category of the monitoring device; the visual scanning device performs a correlation scanning on the detection category of the user's facial surface based on a filter, and performs gray-scale processing on the acquired facial surface state images to obtain facial state indexes;

Preferably, Step S33 specifically includes the following steps:

Step S331: recognizing the gray-scale values and the edges of the facial surface state images based on the detection category, obtaining gray-scale values and coordinate points within the gray-scale range in the facial surface state images, and the monitoring module acquires facial state indexes of a single divided area according to an evaluation formula; and the evaluation formula is expressed as Formula (1):

$$Rr^i = \left(\mu \times \frac{\sum(x^i, y^i) - \sum(x_e^i, y_e^i)}{\sum(x_e^i, y_e^i)}\right) + \left(\lambda \times \frac{\sum(h^i - h_e^i)}{\sum h_e^i}\right) \quad \text{Formula (1)}$$

Formula (1) is used for obtaining a state index Rr' of i area of the facial surface state images in the current detection category of the mark;

in the above formula, $\mu$ and $\lambda$ represents proportion coefficients, $\Sigma(x_e^i, y_e^i)$ represents a sum of coordinate points within the sample gray-scale range in the area marked i, that is, it represents an area of the gray-scale range of the samples, $\Sigma(x^i, y^i)$ represents a sum of image gray-scale coordinate points of the facial surface state in the area marked i $\Sigma(h_e^i-h^i)$ represents a summary of differences between the gray-scale values within the sample gray-scale range and the image gray-scale value of the facial surface state in the area marked i, and $\Sigma h_e^i$ represents a sum of gray-scale values within the sample gray-scale range in the area marked i;

Step S332: repeating Step S331 successively on the n divided areas to obtain a state index of each area; and Step S333: the monitoring module transmits the state index of each area in the user's overall facial surface state image to the determination module.

Preferably, the determination module is used for determining the state index of each area of the user's face, and displaying suggestions for different working modes in the display layer according to the determination results; and the specific working process includes the following steps:

Step S51: the determination module receives the state index of each area from the monitoring module, and determines each state index;

Step S52: when $Rr^i \geq \alpha$, indicating that the state index $Rr^i$ of the facial surface state image of the user in the area marked i is greater than or equals to a state critical value a, that is, the state index does not fall within a normal value range, a superficial facial state in the area marked i does not reach the standards as stated in the samples, in which case, skin beauty is required, and the monitoring module issues a starting command of beauty modes to the control layer and displays the same via the display layer;

Step S53: when $Rr^i < \alpha$ indicating that the state index $Rr^i$ of the facial surface state image of the user in the area marked i is lower than a state critical value $\alpha$, that is, the state index falls within a normal value range, the superficial facial state in the area marked i reaches the standards as stated in the samples, in which case, it is unnecessary to perform skin beauty, and the monitoring module displays a suggestion of not requiring skin beauty via the display layer; and Step S54: the monitoring module extracts the area marks in which skin beauty is required, and transmits the facial positions of the user at which skin beauty is required to the regulation layer.

Preferably, the regulation layer represents a simulation temperature value of the conduction when a light source irradiates facial skin based on a constructed nonlinear transient heat conduction model, and the specific working process includes the following steps:

Step 61: obtaining a temperature value at a coordinate point $(x_f, y_f)$ of each area in the beauty mode according to a temperature conduction formula (2), and the temperature conduction formula (2) is expressed as follows:

$$T(x_f, y_f) = T_i + (\varpi)^{d-1} \times t \times \sum_{o=1}^{d} q_o \times k \times \sqrt{(x_f - x_o)^2 + (y_f - y_o)^2} \quad \text{Formula (2)}$$

Formula (2) is used for acquiring the temperature value $T(x_f, y_f)$ of a skin surface at the coordinate point $(x_f, y_f)$ in a divided area;

in the formula, f represents coordinate point numbers in the divided area, t represents irradiation time of the light source, $q_o$ represents heat emitted by the light source labeled as o in the same divided area, d represents the number of light sources, k represents an effective thermal conductivity coefficient of heat from the light source on the skin surface, $\overline{\omega}$ represents an overlapping attenuation coefficient of the heat from the light source, the coordinate point $(x_o, y_o)$ represents the facial surface state image coordinate corresponding to the light source labeled o in the area, that is the coordinate of the user's skin surface, and $T_i$ represents the normal temperature of the facial surface in the area marked i;

Step 62: bringing each coordinate point in the divided area successively into Step 61 to obtain a temperature value at each coordinate point.

Preferably, the regulation layer constructs a light-heat source model based on Gaussian, the light-heat source model expresses heat of the laser light source through a heat formula, the heat formula includes Formula (3), and Formula (3) is expressed as follows:

$$q = \frac{2\xi P}{\pi w}\exp\left(-\frac{2}{w^2}\right) \quad \text{Formula (3)}$$

Formula (3) is used for obtaining heat emitted by each light sources; in the present disclosure, the laser types used for setting a beauty mode are the same, and the power delivered is also the same, that is, the heat emitted by each laser light source is the same.

In the above formula, P represents power of the laser light source, $\xi$ represents an absorption efficiency of the user's skin to the laser, $\pi$ represents a circumference ratio, W represents a radius of a laser spot, and exp( ) represents an exponential function with a natural constant e as a base.

Preferably, the regulation layer further includes a reaction module, where the reaction module is connected to a filter, and the filter is connected to a counting device; and the specific working process of the reaction module includes the following steps:

Step 81: setting a temperature critical safety value as b, filtering and extracting coordinate points where temperature values exceed b by the filter, and performing numerical value accumulation through the filter by taking 1 as a unit for the extraction of each temperature value;

Step 82: setting a threshold value of an accumulated value of the counting device as m; when the accumulated value of the counting device is greater than or equals to the threshold value m, a warning device connected to the counting device gives a warning, and the working mode of the beauty lamp turns off, so that each laser light source turns off and stops working; and when the accumulated value of the counting device is lower than the threshold value m, the counting device and all laser light sources works normally.

An intelligent regulation and management method includes the following steps:

Step S1: determining whether a user is permitted to log into a system when the user performs user identity identification verification through an automobile central control client or a mobile client, and obtaining access right to the corresponding information according to the user's identity;

Step S2: constructing an actual three-dimensional facial model of the user via a visual scanning device and an ultrasonic measurement device, and dividing various parts of the user's face; where a monitoring module obtains a facial state index of a single divided area according to an evaluation formula, a determination module displays different working mode suggestions in a display layer according to the state index, and the user selects a working mode of a beauty lamp according to the suggestions;

Step S3: in the working process of the beauty lamp, the regulation layer obtains a skin area according to the simulation temperature value of the conduction when the light source irradiates the facial skin and the temperature is too high, and controls the switch of the beauty lamp according to different output results; when the skin area under an excessively high temperature state is less than m, the beauty lamp will work normally; and in other cases, the beauty lamp will be turned off; and Step S4: the display layer displays the completion of working of the beauty lamp.

Preferably, an in-vehicle human body beauty light source, and the in-vehicle human body beauty light source has a light band of 308-1550 nm; and the intelligent regulation and management system for a car beauty lamp is applied in the automobile central control client and adopt an integrated information processing system; the data layer is applied to an automobile central control cloud end, the processing layer and the regulation layer perform cloud end processing based on the automobile central control, the monitoring device is connected to the client end or the automobile central control through a wireless network or wired transmission, and the display layer displays information through a Web page program of an automobile display screen; and a multi-client information architecture is adopted, an independent data group can be established for each user and store the information in the database in a distributed manner, therefore, when a user logs into the system, the system will automatically match and obtain the working data of the historical beauty lamp.

Compared with the Prior Art, the Present Disclosure has the Following Beneficial Effects:

1. The present disclosure adopts the distributed design of the database, the elastic expansion of storage space is achieved, and the running performance of the entire system is improved; by establishing the management design of the user and permissions thereto, restricted access of all users in the same central console is realized to protect the privacy of the user information; the monitoring module in the processing layer constructs the actual three-dimensional facial model of the user based on the facial surface state and the facial skin thickness state of the user, and obtains the facial state index of a single divided area according to the evaluation formula, thereby providing data support for the determination of the determination module; and the determination module determines whether the beauty lamp is suitable for working according to the determination results and provides the user with safety guidance, so as to reduce the skin loss caused by excessive skin beauty.

2. In the present disclosure, the regulation layer constructs a light-heat source model based on Gaussian, the light-heat source model expresses heat of the laser light source through a heat formula, thereby providing data support for a nonlinear transient heat conduction model; the nonlinear transient heat conduction model is used to simulate a temperature value of the conduction when a light source irradiates facial skin, and specific expression of the temperature of the laser beauty lamp that irradiates the facial skin is accordingly realized; and when the skin area under an excessively high temperature state exceeds the safety threshold, the reaction module is used for controlling the operating state of the beauty lamp, such that the safety protection in the working process of the beauty lamp is realized, and the hidden danger of high-temperature burns of the car beauty lamp without medical personnel is solved.

DETAILED DESCRIPTIONS OF THE EMBODIMENTS

Exemplary embodiments according to the present disclosure will be described in detail with reference to the accompanying drawings. Apparently, the described embodiments are merelysome rather than all of the embodiments of the present disclosure. It should be understood that the present disclosure is not limited by the exemplary embodiments described herein.

Embodiment 1

When acting on the human body, lasers from the car beauty lamp will generate heat near the position of body tissues where the lasers are applied, and concentration of a laser light source will also generate heat, the heat generated therefrom, when being diffused onto the human skin, will form a temperature. If the temperature is too high, skin burns will be caused, and the beauty effect will be affected, possibly leading to adverse effects. Furthermore, no medical staff or medicines are scarce during the field operations, and the skin burns may affect the subsequent recovery. Therefore, temperature safety protection is required during the operation of the beauty lamp.

Figure 1:
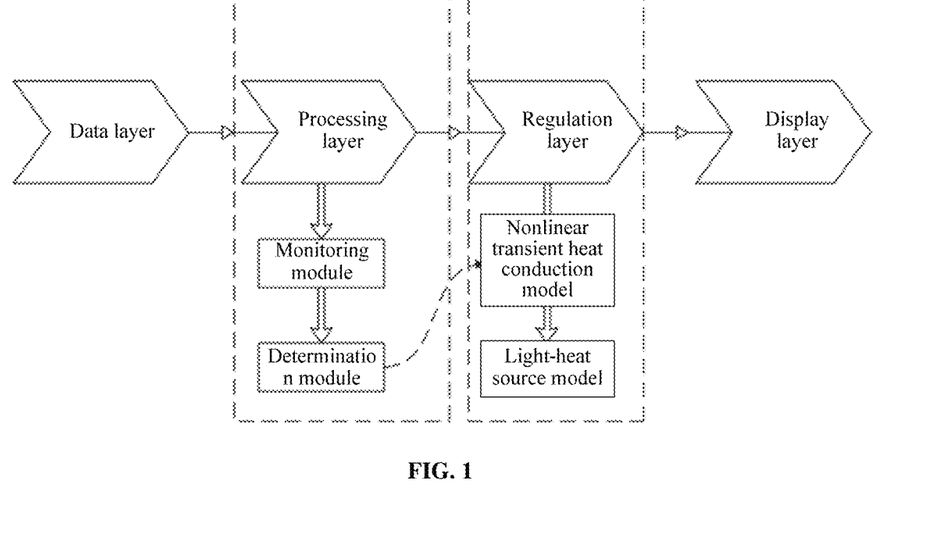
FIG. 1 is a structural schematic diagram of an intelligent regulation and management system for a car beauty lamp provided in the present disclosure.
Figure 2:
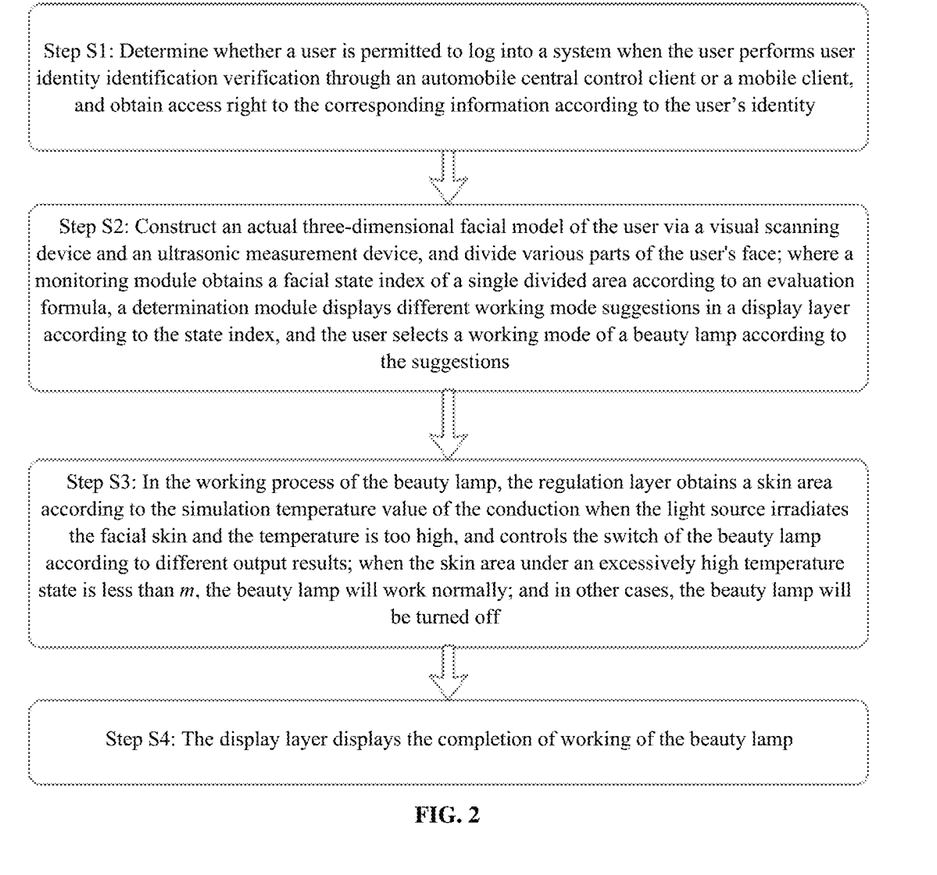
FIG. 2 is a schematic diagram of steps of an intelligent regulation and management method provided in the present disclosure.
Figure 3:
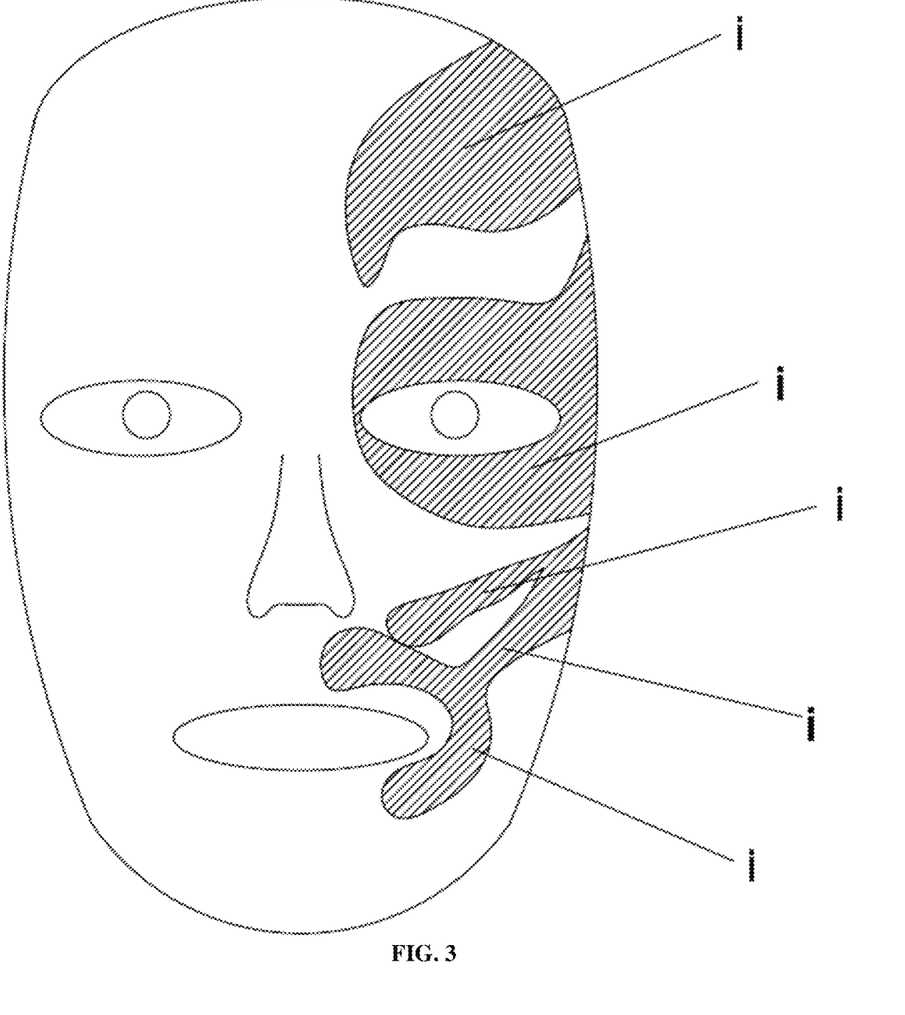
FIG. 3 is a schematic diagram of facial area division in the present disclosure.

With reference to FIGS. 1, 2 and 3, Embodiment 1 further illustrates an intelligent regulation and management system for a car beauty lamp provided in the present disclosure.

An intelligent regulation and management system for a car beauty lamp, including a data layer, a processing layer, a regulation layer and a display layer;

the data layer includes a database and an invoking group, where the data layer and the processing layer are designed based on an NET open source architecture, the database includes a cache of information about the processing layer, a phototherapy laser table and user management information, the phototherapy laser table includes laser wave bands corresponding to each phototherapy, and the database performs distributed storage and invoking management;

the processing layer includes a monitoring module and a determination module, where the monitoring module constructs an actual three-dimensional skin model of a user based on a skin surface state of the user and a skin thickness state of the user, and acquires a skin state index of a single divided region according to an evaluation formula, so as to provide data support for determination of the determination module; and the determination module determines whether the beauty lamp is suitable for working according to the determination results;

the regulation layer acquires a simulation temperature value of the conduction when a light source irradiates facial skin based on a nonlinear transient heat conduction model constructed through a light-heat source model, and controls a working state of the beauty lamp; and the display layer is configured to input and output an application instruction, and display the instruction on a page terminal; and the display layer includes a display device, where the display device accesses an automobile center via a wired interface or a wireless network, and the user inputs a command or an instruction via the page terminal on the display device, such as performing an initial setting of various parameters in a formula or a mode and parameters in other formulas.

The user management information includes a sample pre-stored by the user; the sample is a standard three-dimensional skin model, where the sample includes the skin surface state and the skin thickness state of the user in the most ideal state, and in which case, the skin surface state includes wrinkles, spots and pores; and the skin thickness is only used for calculating a loss state of a collagen layer.

The user management information further includes user identity authentication and permission management, where the user identity authentication is used for user login, and the invoking group checks the identity information inputted by the user when the user logs in against the identity information stored in the database to determine whether the user has the login permission; and the permission management limits the user's access content through a permission model, and assigns corresponding data groups according to the user's authentication identity.

The monitoring module is connected to a monitoring device, and the monitoring module receives facial images of the user in the monitoring device; the monitoring device includes a visual scanning device and an ultrasonic measurement device (the visual scanning device includes a 4D optical imaging of human skin, and completes image shooting including pores, skin lines and wrinkles through a rapid optical non-contact skin imaging system; and the 4D optical imaging of human skin spends 2 min or less on completing measurement in a single area, and resolution of a sensor is greater than or equal to 2×6000×4500 pixel; further, at least four imaging lenses are configured to capture macroscopic and microscopic images of a face, legs, an abdomen, and the like, at the same time; local images of the face, including images of skin lines and wrinkles, can be captured; and they are configured to further capture most areas of the face, including forehead lines, *glabella* lines, eye bag lines, nasolabial folds, and the like, and also to capture changes in a shape and volume of the local or entire face), and the monitoring module is configured to acquire skin states or various parts of the user's face, and specific working process of the monitoring module includes the following steps:

Step S31: the scanning model scans a facial surface state of the user, the ultrasonic measurement device measures a facial skin thickness state of the user, and images of the facial surface state and the facial skin thickness state of the user are combined to construct an actual three-dimensional facial model of the user; and the main process of constructing the three-dimensional facial model includes the following steps: Step 1: establishing a three-dimensional coordinate group according to a facial surface, and taking the facial surface as a reference plane to set a coordinate of each position point on the facial surface to be B(x, y, 0). Step 2: taking the facial surface as a reference plane to set a coordinate of the facial skin thickness to be B(x, y, z); and Step 3: performing reference plane matching on the coordinate of each position point on the facial surface B(x, y, 0) and the coordinate of the facial skin thickness B(x, y, z) to obtain a three-dimensional coordinate of the user's facial model B(x, y, z) where z represents a skin thickness;

Step S32: the monitoring module divides each part of the face based on the actual three-dimensional facial model of the user, it is set that there are n divided areas, and any of the divided areas is marked with i, then $M_i$ means an area divided by the i area; and Step S33: the monitoring module compares the actual three-dimensional facial model of the divided areas with samples in the database, and performs correlation extraction and processing on surface state images of the face according to the detection category of the monitoring device; for example, when the detection category is facial wrinkles, the visual scanning device performs a correlation scanning on the wrinkles of the user's facial surface based on a filter, performs gray-scale processing on the acquired facial surface state images, and a gray-scale deepening degree is used for representing a severity of the wrinkles; the gray-scale deepening degree can be represented by a gray-scale value, edges of the images are recognized through a recognizer, and the edges and within an edge range (within a gray-scale range) are obtained based on the actual three-dimensional facial model for calculating distribution positions of the wrinkles; and when the detection categories are pores, dryness and others, the processing process is also applicable to obtain facial state indexes.

Step S33 specifically includes the following steps:

Step S331: recognizing the gray-scale values and the edges of the facial surface state images based on the detection category, obtaining gray-scale values and coordinate points within the gray-scale range in the facial surface state images, and the monitoring module acquires facial state indexes of a single divided area according to an evaluation formula; and the evaluation formula is expressed as Formula (1):

$$Rr^i = \left(\mu \times \frac{\sum(x^i, y^i) - \sum(x_e^i, y_e^i)}{\sum(x_e^i, y_e^i)}\right) + \left(\lambda \times \frac{\sum(h^i - h_e^i)}{\sum h_e^i}\right) \quad \text{Formula (1)}$$

Formula (1) is used for obtaining a state index $Rr^i$ of i area of the facial surface state images in the current detection category of the mark;

in the above formula, $\mu$ and $\lambda$ represent proportion coefficients, $\Sigma(x_e^i, y_e^i)$ represents a sum of coordinate points within the sample gray-scale range in the area marked i, that is, it represents an area of the gray-scale range of the samples, $\Sigma(x^i, y^i)$ represents a sum of image gray-scale coordinate points of the facial surface state in the area marked i, $\Sigma(h_e^i-h^i)$ represents a summary of differences between the gray-scale values within the sample gray-scale range and the image gray-scale value of the facial surface state in the area marked i, and $\Sigma h_e^i$ represents a sum of gray-scale values within the sample gray-scale range in the area marked i;

Step S332: repeating Step S331 successively on the n divided areas to obtain a state index of each area; and Step S333: the monitoring module transmits the state index of each area in the user's overall facial surface state image to the determination module.

The determination module is used for determining the state index of each area of the user's face, and displaying suggestions for different working modes in the display layer according to the determination results; and the specific working process includes the following steps:

Step S51: the determination module receives the state index of each area from the monitoring module, and determines each state index;

Step S52: when $Rr^i \geq \alpha$, indicating that the state index $Rr^i$ of the facial surface state image of the user in the area marked i is greater than or equals to a state critical value a, that is, the state index does not fall within a normal value range, a superficial facial state in the area marked i does not reach the standards as stated in the samples, in which case, skin beauty is required, and the monitoring module issues a starting command of beauty modes to the control layer and displays the same via the display layer; and an in-vehicle human body beauty light source, the in-vehicle human body beauty light source has a light band of 308-1550 nm.

The beauty modes include whitening, wrinkle removal, pore reduction and moisturizing, each beauty mode corresponds to a color light and light source band, and each detection category can correspond to either a single beauty mode or a plurality of beauty modes; when the monitoring module outputs a result for which beauty is required, the user can select a beauty mode of human body according to the corresponding requirements, including but not limited to:

in a wavelength of 308 nm, human skin, mucous membrane ulcers and pimples are repaired;

in a wavelength of 415 nm-480 nm, human skin inflammation and skin allergy are reduced, and treatment of acnes is required;

in a wavelength of 532 nm, treatment of superficial skin spots such as human skin freckles, age spot (seborrheic keratosis) is required;

in a wavelength of 560 nm, calm and fatigue relieve are required, and human skin roughness is treated;

in a wavelength of 585 nm-590 nm, flow of human lymph is enhanced, and pigmentation inhibition and skin whitening are required in a wavelength of 610 nm-670 nm, human blood circulation is promoted, and acceleration of wound healing, rejuvenation and wrinkle improvement are required;

in wavelengths of 808 nm and 810 nm, human body hair removal, treatment of hairy nevuses, pseudofolliculitis and other skin diseases are treated;

in a wavelength of 830 nm, reduction of human skin pigmentation, skin inflammation relieving and prevention of scar formation are made;

in a wavelength of 850 nm-970 nm, human wounds and scars are prevented or treated;

in a wavelength of 980 nm, formation of new blood vessels in the human body and collagen production are promoted, and inflammation elimination is performed;

in a wavelength of 1050 nm, reduction of sagging and wrinkles of the human skin is performed, and dilation of facial capillaries is improved;

in a wavelength of 1064 nm, epidermal spots, dermal chloasma and pigmentary diseases in people with deep skin color are treated;

in a wavelength of 1450 nm, moderate and severe acnes, folliculitis and sebaceous gland hyperplasia of human skin are treated; and in wavelengths of 1535 nm and 1550 nm, wrinkle removal, skin rejuvenation and depression scars of human skin are treated.

Further, when an LED phototherapy apparatus is used, it should be used no more than 3 times a week and no more than 60 minutes at a time; a wavelength of blue light is close to ultraviolet ray, direct irradiation is easy to damage retina, special protective goggles must be worn, therefore, the display layer is provided with a warning device, where the warning is connected to a counting device, a cycle time of the counting device is one week, that is the counting device performs zero clearing once a week, and cumulative counting is performed within one week after zero clearing; counting rule thereof is that the counting device increases by one for each beauty treatment, and when the value of the counting device increases by three, a warning pop-up window will be displayed when the beauty treatment is performed again, and the user will be warned by a visual machine or warning buzzing whether to wear protective goggles.

Step S53: when $Rr<\alpha$, indicating that the state index $Rr^i$ of the facial surface state image of the user in the area marked i is lower than a state critical value a, that is, the state index falls within a normal value range, the superficial facial state in the area marked i reaches the standards as stated in the samples, in which case, it is unnecessary to perform skin beauty, and the monitoring module displays a suggestion of not requiring skin beauty via the display layer; and Step S54: the monitoring module extracts the area marks in which skin beauty is required, and transmits the facial positions of the user at which skin beauty is required to the regulation layer.

Moderate use of laser beauty can achieve the desired cosmetic effect, excessive use thereof will be counterproductive and may cause skin sensitivity, reduced resistance and other problems, and therefore, the beauty needs to be used moderately. For healthy skin or skin within the range of samples, it is better not to use the laser beauty excessively, and each area of the face has different conditions for the growth of wrinkles and spots, therefore, facial area division is beneficial to targeted treatment.

The specific working process of the monitoring module and the determination module in the processing layer includes the following steps:

Step 1: constructing an actual three-dimensional facial model of the user by combining images of the visual scanning device and the ultrasonic measurement device, dividing various parts of the user's face, setting that there are n divided areas, and any of the divided areas is marked with i;

Step 2: recognizing gray-scale values and gray-scale edges of the actual three-dimensional facial model based on the detection category, the monitoring module gray-scale values and the coordinate points within the gray-scale range to the evaluation formula to obtain facial state indexes of a single divided area; and Step 3: the determination module compares the state indexes with the state critical value to generate a determination result, and outputs the determination result to the display layer or the regulation layer.

In this embodiment, through distributed design of the database, the elastic expansion of storage space is achieved, and the running performance of the entire system is improved; by establishing the management design of the user and permissions thereto, restricted access of all users in the same central console is realized to protect the privacy of the user information; the monitoring module in the processing layer constructs the actual three-dimensional facial model of the user based on the facial surface state and the facial skin thickness state of the user, and obtains the facial state index of a single divided area according to the evaluation formula, thereby providing data support for the determination of the determination module; and the determination module determines whether the beauty lamp is suitable for working according to the determination results and provides the user with safety guidance, so as to reduce the skin loss caused by excessive skin beauty.

Embodiment 2

With reference to FIGS. 1 and 2, Embodiment 2 further illustrates an intelligent regulation and management system for a car beauty lamp provided in the present disclosure.

An intelligent regulation and management system for a car beauty lamp, including a data layer, a processing layer, a regulation layer and a display layer;
(as shown in FIG. 1) the regulation layer represents a simulation temperature value of the conduction when a light source irradiates facial skin based on a constructed nonlinear transient heat conduction model, and the specific working process includes the following steps:

Step 61: obtaining a temperature value at a coordinate point $(x_f, y_f)$ of each area in the beauty mode according to a temperature conduction formula (2), and the temperature conduction formula (2) is expressed as follows:

$$T(x_f, y_f) = T_i + (\varpi)^{d-1} \times t \times \sum_{o=1}^{d} q_o \times k \times \sqrt{(x_f - x_o)^2 + (y_f - y_o)^2} \quad \text{Formula (2)}$$

Formula (2) is used for acquiring the temperature value $T(x_f, y_f)$ of a skin surface at the coordinate point $(x_f, y_f)$ in a divided area;

in the formula, f represents coordinate point numbers in the divided area, t represents irradiation time of the light source, $q_o$ represents heat emitted by the light source labeled as o in the same divided area, d represents the number of light sources, k represents an effective thermal conductivity coefficient of heat from the light source on the skin surface, $\overline{\omega}$ represents an overlapping attenuation coefficient of the heat from the light source, the coordinate point $(x_o, y_o)$ represents the facial surface state image coordinate corresponding to the light source labeled o in the area, that is the coordinate of the user's skin surface, and $T_i$ represents the normal temperature of the facial surface in the area marked i;

Step 62: bringing each coordinate point in the divided area successively into Step 61 to obtain a temperature value at each coordinate point.

Since the beauty lamp is operated by a plurality of laser lamps at the same time in a working state, light from the plurality of laser lamps during irradiation will form a overlapped light diffusion coverage area, the temperature at the overlapping area is not only affected by one laser lamp, the skin surface is beautified by the overlapping influence from the plurality of laser lamps, and the laser mainly uses the heat of light to achieve the purpose of treatment, mainly aiming to improve the appearance of spots or wrinkles on the skin and achieve an improved effect; however, a too high temperature of laser irradiation will cause burns, which will affect the treatment effect, therefore, it is necessary to monitor the irradiation temperature of the laser lamps to reduce the occurrence of facial burns to the user, especially when no doctor is available outdoors and the user selects the beauty mode by herself, special attention needs to be paid to the temperature of the laser lamps.

The regulation layer constructs a light-heat source model based on Gaussian, the light-heat source model expresses heat of the laser light source through a heat formula, the heat formula includes Formula (3), and Formula (3) is expressed as follows:

$$q = \frac{2\xi P}{\pi w} \exp\left(-\frac{2}{w^2}\right) \quad \text{Formula (3)}$$

Formula (3) is used for obtaining heat emitted by each light sources; in the present disclosure, the laser types used for setting a beauty mode are the same, and the power delivered is also the same, that is, the heat emitted by each laser light source is the same.

In the above formula, P represents power of the laser light source, $\xi$ represents an absorption efficiency of the user's skin to the laser, $\pi$ represents a circumference ratio, W represents a radius of a laser spot, and exp( ) represents an exponential function with a natural constant e as a base.

The regulation layer further includes a reaction module, where the reaction module is connected to a filter, and the filter is connected to a counting device; and the specific working process of the reaction module includes the following steps:

Step 81: setting a temperature critical safety value as b, filtering and extracting coordinate points where temperature values exceed b by the filter, and performing numerical value accumulation through the filter by taking 1 as a unit for the extraction of each temperature value; and an accumulation period of the counting device is the working time of a single beauty mode, when the single beauty mode stops working, the counting device performs zero clearing, the numerical value of the counting device can also represent an area formed by the accumulation of coordinate points an excessively high temperature values, that is, the area with excessively high temperature value of the user's skin surface.

Step 82: setting a threshold value of an accumulated value of the counting device as m; when the accumulated value of the counting device is greater than or equals to the threshold value m, a warning device connected to the counting device gives a warning, and the working mode of the beauty lamp turns off, so that each laser light source turns off and stops working; and when the accumulated value of the counting device is lower than the threshold value m, the counting device and all laser light sources work normally.

An intelligent regulation and management method mainly includes the following steps:

Step S1: determining whether a user is permitted to log into a system when the user performs user identity identification verification through an automobile central control client or a mobile client, and obtaining access right to the corresponding information according to the user's identity;

Step S2: constructing an actual three-dimensional facial model of the user via a visual scanning device and an ultrasonic measurement device, and dividing various parts of the user's face; where a monitoring module obtains a facial state index of a single divided area according to an evaluation formula, a determination module displays different working mode suggestions in a display layer according to the state index, and the user selects a working mode of a beauty lamp according to the suggestions;

Step S3: in the working process of the beauty lamp, the regulation layer obtains a skin area according to the simulation temperature value of the conduction when the light source irradiates the facial skin and the temperature is too high, and controls the switch of the beauty lamp according to different output results; when the skin area under an excessively high temperature state is less than m, the beauty lamp will work normally; and in other cases, the beauty lamp will be turned off; and Step S4: the display layer displays the completion of working of the beauty lamp.

The intelligent regulation and management system for a car beauty lamp and the in-vehicle human body beauty light source are applied in the automobile central control client and adopt an integrated information processing system; the data layer is applied to an automobile central control cloud end, the processing layer and the regulation layer perform cloud end processing based on the automobile central control, the monitoring device is connected to the client end or the automobile central control through a wireless network or wired transmission, and the display layer displays information through a Web page program of an automobile display screen; and a multi-client information architecture is adopted, an independent data group can be established for each user and store the information in the database in a distributed manner, therefore, when a user logs into the system, the system will automatically match and obtain the working data of the historical beauty lamp and save the skin state data of each time the beauty lamp works, so that the user can observe the samples and obtain the beauty effect.

In this embodiment, the regulation layer constructs a light-heat source model based on Gaussian, the light-heat source model expresses heat of the laser light source through a heat formula, thereby providing data support for a nonlinear transient heat conduction model; the nonlinear transient heat conduction model is used to simulate a temperature value of the conduction when a light source irradiates facial skin, and specific expression of the temperature of the laser beauty lamp that irradiates the facial skin is accordingly realized; and when the skin area under an excessively high temperature state exceeds the safety threshold, the reaction module is used for controlling the operating state of the beauty lamp, such that the safety protection in the working process of the beauty lamp is realized, and the hidden danger of high-temperature burns of the car beauty lamp without medical personnel is solved.

It should be noted that the present disclosure relates to a control system for human body beauty and a light source for emitting light for an automobile, and is not limited to facial beauty only.

In addition, each functional unit in the various embodiments of the present disclosure can be integrated into a processing unit, or an individual unit can physically exist alone, or two or more units can be integrated into a single unit.

What is described above is merely the preferred implementation of the present disclosure, the scope of protection of the present disclosure is not limited to the above embodiments, and all technical solutions following the idea of the present disclosure fall within the scope of protection of the present disclosure. It should be noted that several modifications and adaptations made by those of ordinarily skilled in the art without departing from the principle of the disclosure should also fall within the scope of protection of the disclosure.

What it claimed is:

1. An intelligent regulation and management system for a car beauty lamp, comprising a data layer, a processing layer, a regulation layer and a display layer;

the data layer comprises a database and an invoking group, wherein the data layer and the processing layer are designed based on an NET open source architecture, the database comprises a cache of information about the processing layer, a phototherapy laser table and user management information, the phototherapy laser table comprises laser wave bands corresponding to each phototherapy, and the database performs distributed storage and invoking management;

the processing layer comprises a monitoring module and a determination module, wherein the monitoring module constructs an actual three-dimensional skin model of a user based on a skin surface state of and a skin thickness state of the user, and acquires a skin state index of a single divided region according to an evaluation formula, so as to provide data support for determination of the determination module; and the determination module determines whether the beauty lamp is suitable for working according to the determination results;

the regulation layer acquires a simulation temperature value of the conduction when a light source irradiates facial skin based on a nonlinear transient heat conduction model constructed through a light-heat source model, and controls a working state of the beauty lamp; and the display layer is configured to input and output an application instruction, and display a page terminal.

2. The intelligent regulation and management system for a car beauty lamp according to claim 1, wherein the user management information comprises a sample pre-stored by the user, and the sample is a standard three-dimensional skin model; and the user management information further comprises user identity authentication and permission management, wherein the user identity authentication is used for user login, and the invoking group checks the identity information inputted by the user when the user logs in against the identity information stored in the database to determine whether the user has the login permission; and the permission management limits the user's access content through a permission model, and assigns corresponding data groups according to the user's authentication identity.

3. The intelligent regulation and management system for a car beauty lamp according to claim 1, wherein the monitoring module is connected to a monitoring device, and the monitoring module receives facial images of the user in the monitoring device; the monitoring device comprises a visual scanning device and an ultrasonic measurement device, the monitoring module is configured to acquire skin states or various parts of the user's face, and specific working process of the monitoring module comprises the following steps:

Step S31: the scanning model scans a facial surface state of the user, the ultrasonic measurement device measures a facial skin thickness state of the user, and images of the facial surface state and the facial skin thickness state of the user are combined to construct an actual three-dimensional facial model of the user;

Step S32: the monitoring module divides each part of the face based on the actual three-dimensional facial model of the user, it is set that there are n divided areas, and any of the divided areas is marked with i, then $M_i$ means an area divided by the i area; and Step S33: the monitoring module compares the actual three-dimensional facial model of the divided areas with samples in the database, and performs correlation extraction and processing on surface state images of the face according to the detection category of the monitoring device to obtain facial state indexes.

4. The intelligent regulation and management system for a car beauty lamp according to claim 3, wherein Step S33 specifically comprises the following steps:

Step S331: recognizing the gray-scale values and the edges of the facial surface state images based on the detection category, obtaining gray-scale values and coordinate points within the gray-scale range in the facial surface state images, and the monitoring module acquires facial state indexes of a single divided area according to an evaluation formula; and the evaluation formula is expressed as Formula (1):

$$Rr^i = \left(\mu \times \frac{\sum(x^i, y^i) - \sum(x_e^i, y_e^i)}{\sum(x_e^i, y_e^i)}\right) + \left(\lambda \times \frac{\sum(h^i - h_e^i)}{\sum h_e^i}\right) \quad \text{Formula (1)}$$

Formula (1) is used for obtaining a state index $Rr^i$ of i area of the facial surface state images in the current detection category of the mark;

in the above formula, U and A represent proportion coefficients, $\Sigma(x_e^i, y_e^i)$ represents a sum of coordinate points within the sample gray-scale range in the area marked i, that is, it represents an area of the gray-scale range of the samples, $\Sigma(x^i, y^i)$ represents a sum of image gray-scale coordinate points of the facial surface state in the area marked i, $\Sigma(h_e^i - h^i)$ represents a summary of differences between the gray-scale values within the sample gray-scale range and the image gray-scale value of the facial surface state in the area marked i, and $\Sigma h_e^i$ represents a sum of gray-scale values within the sample gray-scale range in the area marked i;

Step S332: repeating Step S331 successively on the n divided areas to obtain a state index of each area; and Step S333: the monitoring module transmits the state index of each area in the user's overall facial surface state image to the determination module.

5. The intelligent regulation and management system for a car beauty lamp according to claim 4, wherein the determination module is used for determining the state index of each area of the user's face, and displaying suggestions for different working modes in the display layer according to the determination results; and the specific working process comprises the following steps:

Step S51: the determination module receives the state index of each area from the monitoring module, and determines each state index;

Step S52: when $Rr^i \geq \alpha$, indicating that the state index $Rr^i$ of the facial surface state image of the user in the area marked i is greater than or equals to a state critical value α, that is, the state index does not fall within a normal value range, a superficial facial state in the area marked i does not reach the standards as stated in the samples, in which case, skin beauty is required, and the monitoring module issues a starting command of beauty modes to the control layer and displays the same via the display layer; and Step S53: when $Rr^i < \alpha$, indicating that the state index $Rr^i$ of the facial surface state image of the user in the area marked i is lower than a state critical value α, that is, the state index falls within a normal value range, the superficial facial state in the area marked i reaches the standards as stated in the samples, in which case, it is unnecessary to perform skin beauty, and the monitoring module displays a suggestion of not requiring skin beauty via the display layer; and Step S54: the monitoring module extracts the area marks in which skin beauty is required, and transmits the facial positions of the user at which skin beauty is required to the regulation layer.

6. The intelligent regulation and management system for a car beauty lamp according to claim 5, wherein the regulation layer represents a simulation temperature value of the conduction when a light source irradiates facial skin based on a constructed nonlinear transient heat conduction model, and the specific working process comprises the following steps:

Step 61: obtaining a temperature value at a coordinate point $(x_f, y_f)$ of each area in the beauty mode according to a temperature conduction formula (2), and the temperature conduction formula (2) is expressed as follows:

$$T(x_f, y_f) = T_i + (\varpi)^{d-1} \times t \times \sum_{o=1}^{d} q_o \times k \times \sqrt{(x_f - x_o)^2 + (y_f - y_o)^2}$$

Formula (2)

Formula (2) is used for acquiring the temperature value T $(x_f, y_f)$ of a skin surface at the coordinate point $(x_f, y_f)$ in a divided area;

in the above formula, f represents coordinate point numbers in the divided area, t represents irradiation time of the light source, $q_o$ represents heat emitted by the light source labeled as o in the same divided area, d represents the number of light sources, k represents an effective thermal conductivity coefficient of heat from the light source on the skin surface, $\overline{\omega}$ represents an overlapping attenuation coefficient of the heat from the light source, the coordinate point $(x_o, y_o)$ represents the facial surface state image coordinate corresponding to the light source labeled o in the area, that is the coordinate of the user's skin surface, and $T_i$ represents the normal temperature of the facial surface in the area marked i;

Step 62: bringing each coordinate point in the divided area successively into Step 61 to obtain a temperature value at each coordinate point.

7. The intelligent regulation and management system for a car beauty lamp according to claim 6, wherein the regulation layer constructs a light-heat source model based on Gaussian, the light-heat source model expresses heat of the laser light source through a heat formula, the heat formula comprises Formula (3), and Formula (3) is expressed as follows:

$$q = \frac{2\xi P}{\pi w} \exp\left(-\frac{2}{w^2}\right)$$

Formula (3)

Formula (3) is used for obtaining heat emitted by each light sources; and in the above formula, P represents power of the laser light source, $\xi$ represents an absorption efficiency of the user's skin to the laser, $\pi$ represents a circumference ratio, w represents a radius of a laser spot, and exp( ) represents an exponential function with a natural constant e as a base.

8. The intelligent regulation and management system for a car beauty lamp according to claim 7, wherein the regulation layer further comprises a reaction module, the reaction module is connected to a filter, and the filter is connected to a counting device; and the specific working process of the reaction module comprises the following steps:

Step 81: setting a temperature critical safety value as b, filtering and extracting coordinate points wherein temperature values exceed b by the filter, and performing numerical value accumulation through the filter by taking 1 as a unit for the extraction of each temperature value;

Step 82: setting a threshold value of an accumulated value of the counting device as m; when the accumulated value of the counting device is greater than or equals to the threshold value m, a warning device connected to the counting device gives a warning, and the working mode of the beauty lamp turns off, so that each laser light source turns off and stops working; and when the accumulated value of the counting device is lower than the threshold value m, the counting device and all laser light sources works normally.

9. An in-vehicle human body beauty light source, wherein the in-vehicle human body beauty light source is equipped with the intelligent regulation and management system for a car beauty lamp according to claim 1, and the in-vehicle human body beauty light source has a light band of 308-1550 nm.

\* \* \* \* \*